United States Patent [19]

Nicklaus et al.

[11] 4,357,300

[45] Nov. 2, 1982

[54] APPARATUS FOR PROCESS ANALYSIS

[75] Inventors: Eberhard Nicklaus, Bergheim; Heinz Warncke, Cologne; Wilhelm Pross; Wolfgang Härtl, both of Munich, all of Fed. Rep. of Germany

[73] Assignees: Bayer Aktiengesellschaft, Leverkusen; Compur-Electronic GmbH, Munich, both of Fed. Rep. of Germany

[21] Appl. No.: 154,341

[22] Filed: May 29, 1980

[30] Foreign Application Priority Data

Jun. 11, 1979 [DE] Fed. Rep. of Germany ....... 2923627

[51] Int. Cl.³ ...................... G01N 35/08; G06F 15/42
[52] U.S. Cl. ........................................ 422/62; 422/67; 364/497; 364/178
[58] Field of Search ................. 23/230 A; 422/62, 67; 364/500, 105, 497

[56] References Cited

U.S. PATENT DOCUMENTS 3,932,132  1/1976  Hijikata ............................ 422/67 X
3,960,497  6/1976  Acord .................................. 422/67
4,043,756  8/1977  Sommervold .................... 422/67 X Primary Examiner—Ronald Serwin
Attorney, Agent, or Firm—Sprung, Felfe, Horn, Lynch & Kramer

[57] ABSTRACT

In an apparatus for process analysis, a test substance is removed from the process stream by a probe and fed to an analysis instrument with a measured value display. Upstream of the analysis instrument, the test gas is conveyed through condensers. A monitoring unit is coupled to the analysis instruments and the processing chain without influencing the flow of data from the analysis instrument to the measured value display. The monitoring unit receives information about the entire apparatus via status sensors which are incorporated into the processing chain and into the analysis instrument. Depending on this information, the monitoring unit can intervene via solenoid valves, switches and motor potentiometers into the apparatus and alter its operation. The condition of the apparatus can also be displayed.

4 Claims, 2 Drawing Figures

APPARATUS FOR PROCESS ANALYSIS

BACKGROUND OF THE INVENTION

The invention relates to an apparatus for the continuous or quasi-continuous analysis of test substances, which presents a closed system in that all external intervention can be avoided, provided that it is not necessitated by failure indications. If indications of failure do not throw the measured values produced into doubt, the measured values can be considered to be reliable. Routine operations (calibration, condensate delivery from a test gas condenser, blow-through of an extraction probe and the like) are carried out automatically. The test substances can be present in a gaseous or liquid phase.

Process analysis measuring devices consist of an extraction device, a processing chain and at least one analysis instrument, the individual parts being designed in different ways depending on the object set. For example, the extraction device and processing chain are generally very simple in design for monitoring environmental air whereas they are usually of quite a complex configuration for measuring emission. The functioning of the analysis instrument is normally dependent upon the correct functioning of the extraction device and the processing chain. In process analysis measuring devices it is important for the measured values to be readily available and reliable. Up until now, daily checks of operation have generally been carried out by skilled workers to achieve sufficient availability and reliability. The analysis instruments are calibrated regularly to maintain the accuracy of measurement. This method of preventive maintenance has the disadvantage, in addition to the associated high cost, that disturbances occurring between two checks of operation can remain unnoticed. This applies, in particular, to those disturbances which do not affect the measurement value (for example, insufficient permeation of test gas due to a blockage).

In the past, it has been proposed that the availability of analysis measurements be increased while simultaneously reducing the operating costs by using process computers. In this arrangement, the conditions of status sensors should be transmitted to a measuring device and the measured value to a central computer which examines the plausibility of the measured value and checks the operation of the measuring device using the status indications. The computer should be able to intervene in the measuring device and, for example, effect calibration by remote control.

This design is only suitable for extensive measuring networks due to the associated cost (computer software, remote control system). Moreover, in principle, both the computer and remote control system threaten the availability of the measured values.

Due to this fact, this design has hitherto only been adopted in environmental protection measuring networks as far as we know.

There are some analysis instruments which indicate deviations from the desired operating condition by means of status displays. There are also auxiliary devices which carry out calibration according to a fixed time program or are initiated from outside. In this case, the analysis instrument is charged with null gas or sensitivity gas. In certain conventional commercial instruments, the measured values determined are stored and the following measured values are corrected electronically on the basis of the stored calibration values. The disadvantage of this method is that the measured value is transposed into a correction circuit. If this is absent, the measured value is not available. Although a failure indication is produced in these automatic balancing devices when the calibration values have drifted from a certain range, undetectable operating conditions in which incorrect values are stored can exist. In another instrument, which is marketed in conjunction with IR analysis devices, the zero point and sensitivity are adjusted on the analysis instrument by means of motor potentiometers. Although the measured value is not hereby corrected, defective adjustments are not identified by failure indications.

The apparatuses just described have the disadvantage that only parts of the measuring device are monitored (status displays on analysis instruments) or only parts of the routine operations are automated (automatic equalization devices), the availability of the latter being impaired in principle by transposition of the measured value and/or irregular calibrations not being identified externally during routine operations.

SUMMARY OF THE INVENTION

An object of the invention is to increase the availability of process analysis measuring devices and to reduce the maintenance costs.

This object is achieved according to the invention in that a conventional type of measuring device is provided with a monitoring unit which receives information about the entire measuring device by means of status sensors and from the measured values and intervenes in the measuring device by means of solenoid valves, switches and motor potentiometers and emits messages about the condition of the measuring device to the exterior. The number of measured values prevent the availability of the measured values from being impaired by the monitoring unit.

The measured values are passed via a passive component and are not changed directly but by means of motorised adjusting potentiometers on the analysis instruments. Suitable definitions of the outputs of the monitoring unit allow the measuring device to assume its generally measurable basic condition in the absence thereof and to emit a failure indication to the exterior. At any time, the measuring device can be operated quite simply by actuating a switch in the as yet conventional manner and without the possibility of intervening in the monitoring unit.

The measuring device is monitored by checking the condition of the status sensors and by continuously examining the plausibility of the measured value. If a disturbance occurs, failure indications are emitted to the exterior and, if possible, an intervention is made into the measuring device in such a way that the disturbance is removed or at least partially compensated. The disturbance can be removed by connecting a reserve component. Routine maintenance measures (for example, calibration) are carried out according to a fixed time program, whereby faults which may occur are identified in the form of failure indications.

BRIEF DESCRIPTION OF THE DRAWINGS

The invention is described in more detail below with reference to an embodiment shown in the drawings wherein.

DETAILED DESCRIPTION OF THE INVENTION

Figure 1:
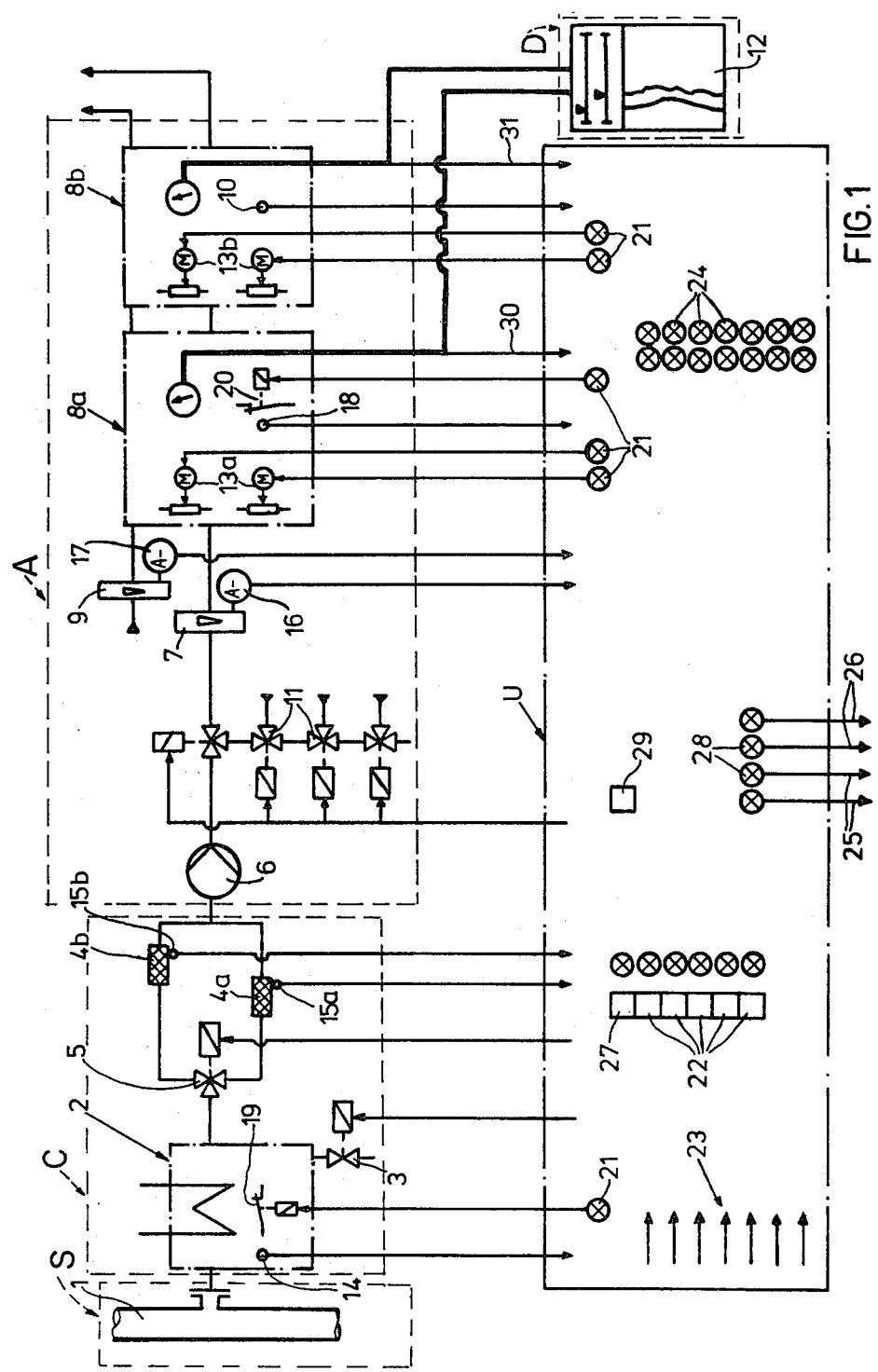
FIG. 1 is a schematic representation of the apparatus and FIG. 2 is a flow chart of the process steps.

According to FIG. 1 test gas is removed from an operating line by a probe 1 (extraction device) and conveyed through a test gas condenser 2. The condensate produced can be discharged by means of a valve 3. The test gas is subsequently dried in an absorber 4a, whereby a reserve absorber 4b can be connected with the aid of a valve 5. A pump 6 conveys the test gas through a flow meter 7 and to analysis instruments 8a, 8b which are rinsed by a protective gas whose flow is checked by a flow meter 9. The test gas condenser 2 and absorber 4a and 4b form the processing chain connected upstream of the analysis instruments 8a and 8b and their measured value display 12. The first analysis instrument 8a should have a thermostat 18 and the second 8b a status display 10. By using a valve combination 11, it is possible to convey search gases (null or sensitivity gas) through the analysis instruments instead of test gas. The measured values in the analysis instruments are displayed on a recorder 12 and registered. Zero and sensitivity can be adjusted by potentiometers 13a, 13b.

This measuring device is equipped with the following status sensors: thermometers 14 for test gas condenser temperature; sensors 15a, 15b for the condition of the absorbers; minimal contacts 16, 17 on the flowmeters 7, 9; thermometer 18 for analysis instrument temperature control, status display 10 on the analysis instrument 8b. All status sensors are connected to a central monitoring unit U. Unlike the known instruments, it is coupled to the processing chain and the analysis instruments in a type of shunt. This prevents the data flow from the analysis instruments 8a, 8b to the measured value display 12 from being obstructed. Moreover, the monitoring unit can, in passing, be disconnected from the measuring device in this way without impairing the fundamental operation of the analysis measuring device. The monitoring unit U receives other information directly from the measured values (lines 30, 31).

The monitoring unit U can connect all valves which shift adjusting potentiometers and disconnect the current supplies of the test gas condenser and the thermostat with relays 19, 20. The condition of these outputs is displayed on the monitoring unit by light-emitting diodes 21. The valves can also be controlled manually by switches 22.

A total of seven internally adjustable voltages 23 allows the monitoring unit U to be adapted to a variety of measuring devices. The desired values for the zero point and sensitivity adjustments of the analysis instruments, the permitted variation in the measured values and the lower limit to the measuring range (for checking plausibility) can be selected at random. When monitoring the temperature, the upper limit of the permitted temperature range can be predetermined, the monitoring unit U ascertaining from the magnitude of these limit values whether a condenser or a thermostat is to be checked. Voltage supplies can be disconnected accordingly, depending on whether under-cooling or over-heating is established. The desired values for the sensitivity adjustments similarly indicate how many analysis instruments are to be monitored and calibrated.

Disturbances are indicated internally in different ways, depending on their cause, by light-emitting diodes 24. External failure indications are emitted overall in two stages ("warning" "measurement absent") in the form of potential-free contacts 25. Two other externally usable messages 26 identify the operating condition of the measuring device. "Calibration" is indicated if the measuring device is occupied with itself and the measured values are not available. "Maintenance" is indicated if the maintenance switch 27 is pressed. If that is so, the measuring device runs by manual operation, i.e. the monitoring unit is disconnected from the rest of the measuring device. All externally usable messages are represented internally by light-emitting diodes 28.

A micro-processor which jumps to the beginning of the program fed into it upon actuation of switch 29, is contained as a central component in the monitoring unit U.

Figure 2:
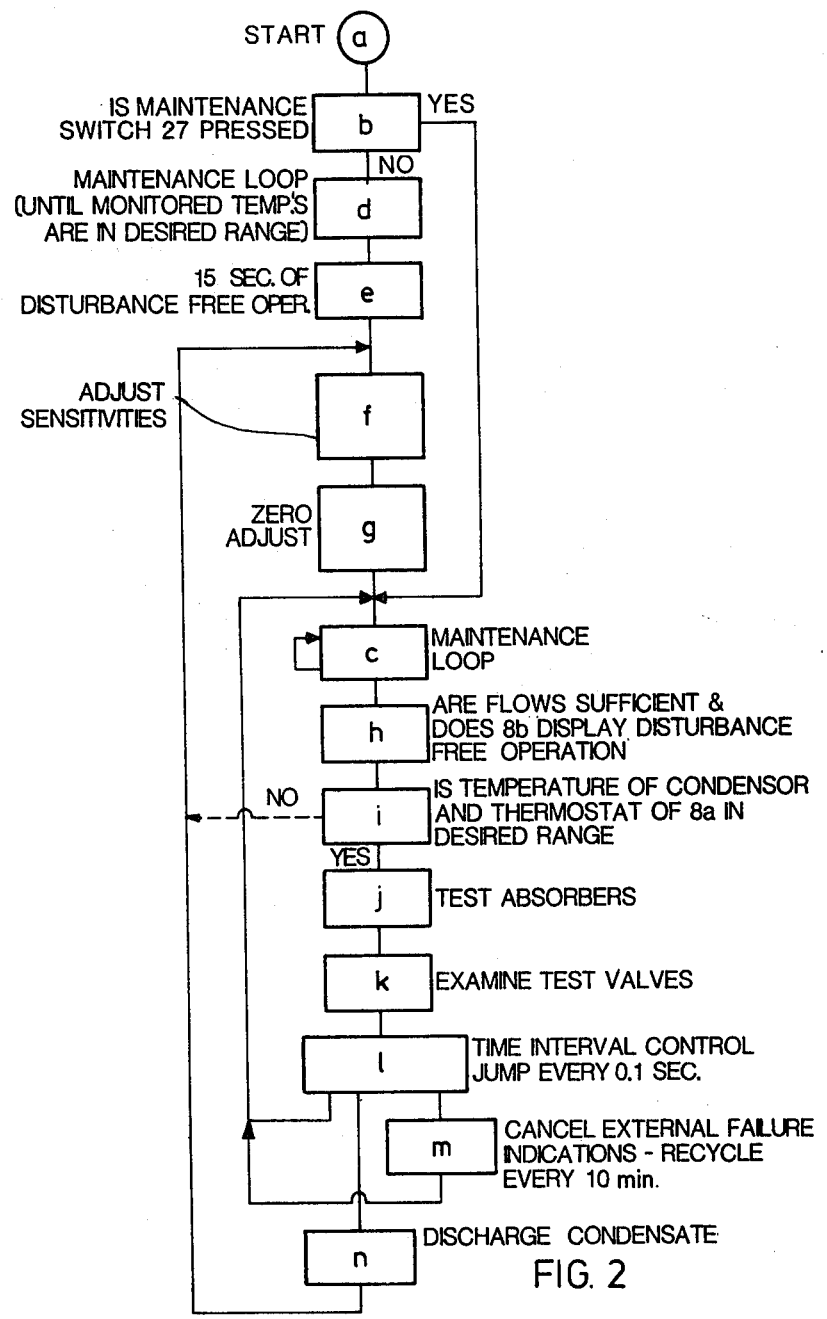

FIG. 2 shows the functioning of the monitoring unit in the form of a flow chart.

Once the voltage has been switched on or the switch 29 actuated (FIG. 1), the system jumps from the starting point a to b then examines whether the maintenance switch 27 (FIG. 1) is pressed. If this is so, the system remains in a maintenance loop c in which the monitoring unit is disconnected and the rest of the measuring device situated in its basic condition. If the maintenance switch is not pressed, the system remains in maintenance loop d until the temperatures to be monitored lie within the desired range. In the next portion e, an examination is made to see whether the status display of the analysis instrument 8b, FIG. 1, signals disturbance-free operation uninterruptedly for at least 15 seconds.

The portion "adjust sensitivities" f follows. The analysis instruments are traversed in succession with sensitivity gas (gas of known concentration) with the aid of the valve combination 11. After a rinsing period, the flowmeter 7 and its minimum contact 16 are used to check whether sensitivity gas is flowing through the analysis instruments. If not, failure indications are emitted. If so, the measured value of the analysis instrument to be adjusted is brought step-wise to the predetermined desired value with the aid of a sensitivity motor potentiometer. If more than 32 steps are needed or if the direction of adjustment has to be changed more than twice, adjustment is interrupted and failure indications are emitted. The zeros are adjusted accordingly in the following portion g.

The measured value is not available during the adjustments. This is announced externally by the message "calibration". This message is retracted only after sufficiently long rinsing with test gas.

If the maintenance switch 27 is pressed in portion c, all failure indications are cancelled, the rest of the measuring device is shifted into its basic condition, and the monitoring unit is disconnected. If the maintenance switch is only actuated briefly, the program jumps into the portions f and g (calibration).

A check as to whether the flows are sufficiently large and whether the status display of the analysis instrument 8b displays disturbance-free operation is carried out in portion h. A check is carried out in portion i as to whether the temperatures of the test gas condenser and the thermostat of the analysis instrument 8a lie in the desired range. If the desired range is fallen below or exceeded, the voltage supplies are disconnected. If the thermostat temperature does not lie in the desired range, adjustments are made hourly to compensate zero and sensitivity drifts.

The condition of the absorbers 4a and 4b is examined in portion j. If the absorber 4a is exhausted, the reserve absorber 4b is connected by the solenoid valve 5. If both absorbers are exhausted, the test gas is disconnected to protect the analysis instrument.

The plausibility of the test values is examined in portion k. If they lie outside the measuring range or their variation exceeds that allowed by a predetermined range of variation, messages are emitted, as in the case of all other disturbances. Depending on the effect of a failure on the measured values, "warning" or "measurement absent" is indicated externally.

The time interval of the other portions is controlled in the time branches 1. The program jumps to portion c every 0.1 seconds. A temporal delay is incorporated so that variations having frequencies of 10 Hz can be detected when examining plausibility.

The external failure indications are initially cancelled every 10 minutes in portion m if they do not originate from portions f or g (calibration). They are produced again in the following one if the causes of the failure are still present. The external failure indications are thus up-dated.

Portion n (condensate discharged) with which the condensate produced in the test gas condenser is discharged by actuation of the solenoid valve 3 is inserted every 24 hours or 168 hours. As the measured values are not available in this process, the external output "calibration" is positioned during this operation. Portions f and g (calibration) follow n.

We claim:

1. In an apparatus for process analysis having means for continuously extracting a sample from a process stream, means for conditioning the sample, at least one sample analyzer and a measurement display, the improvement comprising: sensors connected to at least the sample conditioning means and the sample analyzer for producing electrical signals responsive to the functional status thereof and monitoring means coupled with its inputs to the outputs of the status sensors in parallel with respect to at least the sample conditioning means and the analyzer for monitoring the analysis without affecting the data flow from the analyzer to the measurement display, the monitoring means comprising (a) a first circuit for checking the operational status of at least the sample conditioning means and the analyzer via the status sensors,
(b) a second circuit for checking the plausibility of the measured value received from the analyzer and
(c) a third circuit for indicating a failure in response to the recognition by the first and second circuits of a deviation from a desired predetermined range.

2. The apparatus according to claim 1, wherein the monitoring means further comprises a fourth circuit for adjusting the zero point and the sensitivity of the analyzer.

3. The apparatus according to claim 2, wherein the sample conditioning means comprises reserve components and wherein the monitoring means further comprises a fifth circuit for connecting a reserve component in the sample flow in response to the failure of an already connected component.

4. The apparatus according to claim 2 or claim 3, wherein the monitoring means further comprises a sixth circuit for indicating that the measured values are reliable after an absence of a voltage supply in response to the resumption of desired conditions in the sample conditioning means and analyzer.

* * * * *